United States Patent [19]

Hempel et al.

[11] Patent Number: 5,505,738
[45] Date of Patent: Apr. 9, 1996

[54] SURGICAL SAW

[75] Inventors: Dietrich Hempel, Hamburg; Harm-Iven Jensen, Kiel, both of Germany

[73] Assignee: Howmedica GmbH, Schoenkirchen, Germany

[21] Appl. No.: 179,404

[22] Filed: Jan. 10, 1994

[30] Foreign Application Priority Data

Jan. 12, 1993 [DE] Germany ............................ 9300271 U

[51] Int. Cl.[6] ............................ A61B 17/14; A61B 17/32
[52] U.S. Cl. ............................ 606/82; 606/170; 606/176; 30/504; 30/517
[58] Field of Search ............................ 606/82, 170, 79, 606/171, 172, 177, 178, 176; 30/166.3, 504, 505, 514, 517

[56] References Cited

U.S. PATENT DOCUMENTS

| 769,829 | 9/1904 | Mott | 606/171 |
|---|---|---|---|
| 3,468,312 | 9/1969 | Küntscher . | |
| 3,472,229 | 10/1969 | Küntscher . | |
| 3,678,934 | 7/1972 | Warfield et al. | 606/79 |
| 3,943,934 | 3/1976 | Bent | 606/178 |
| 3,952,412 | 4/1976 | Rhodes . | |
| 3,967,377 | 7/1976 | Wells | 606/170 |
| 4,633,860 | 1/1987 | Korth et al. | 606/170 |
| 4,976,031 | 12/1990 | Miller | 30/166.3 |
| 5,293,878 | 3/1994 | Bales et al. | 606/170 |

FOREIGN PATENT DOCUMENTS 1050383   12/1966   United Kingdom .

OTHER PUBLICATIONS

"Closed Intramedullary Shortening of the Femur" by Robert Winquist et al, Clinical Orthopedics & Related Research, No. 136, Oct. 1978, pp. 54–61.

*Primary Examiner*—Stephen C. Pellegrino
*Assistant Examiner*—Scott B. Markow
*Attorney, Agent, or Firm*—Peter C. Richardson; Lawrence C. Akers; Elizabeth O. Slade

[57] ABSTRACT

A surgical saw has a sector-shaped saw blade mounted on a shaft. The shaft is surrounded by a coaxial second shaft to which an eccentric member is mounted close to a saw blade and parallel therewith. Both shafts and thus the eccentric member and the cutting blade can be rotated with respect to each other and can be fixed in their rotational position. Depending on the rotational position, the saw blade is either covered by the eccentric member in a rest position to be inserted in a hollow bone, or is indexed in a position to be freely and gradually exposed to make a sawing operation possible.

5 Claims, 3 Drawing Sheets

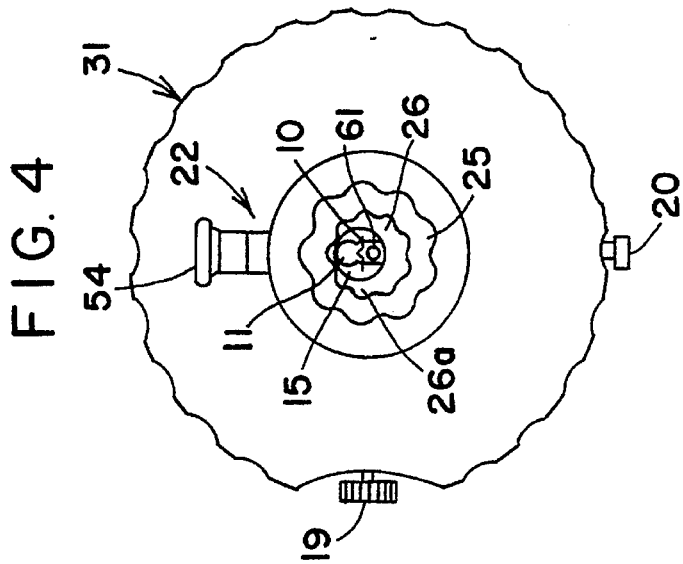
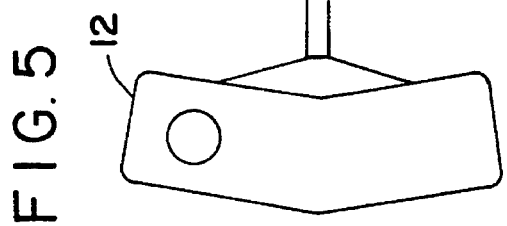
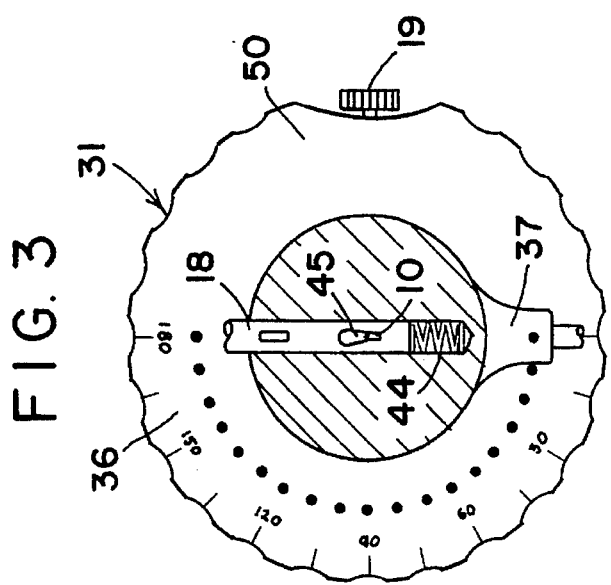

SURGICAL SAW

BACKGROUND OF THE INVENTION

1. Field of the Invention

The present invention relates to a surgical caw capable of cutting a bone from the inside towards the outside thereof.

2. Description of the Prior Art

German patent DE 28 49 760 discloses an oscillating surgical saw comprising a saw blade mounted on the end of a shaft to make a cut in a plane perpendicular to the shaft. The shaft is driven by a motor and designed in combination with the cutting blade such that only low pressure acting in the direction of feed is needed. This type of saw is suited to cut bone material when the saw is applied to the bone from outside rather than the inside as contemplated by the present invention. The shaft including the saw blade is particularly short to facilitate an accurate guiding of the saw in particular with respect to the cutting depth. The cutting depth is visually controlled or adjusted by the surgeon.

As a visual control of the cutting operation is necessary and with respect to the short sawing shaft necessary for manual guidance, a sawing operation in the inner space of a hollow bone is not possible using this type of saw.

A saw designed to cut a bone from the inside out is discussed in an article entitled "Closed Intramedullary Shortening of the Femur" by Robert A. Winquist et al in Clinical Orthopedics and Related Research, number 136, October 1978.

SUMMARY OF THE INVENTION

It is an object of the present invention to provide a surgical saw which is suited to make cuts in the inner space or canal of a hollow bone.

According to the invention, a saw head mounted to the end of both coaxial shafts is defined by a saw blade in combination with the eccentric member, each one being connected to one of the shafts. Rotating one shaft with respect to the other, changes the radial range of the saw head. When the eccentric member extends in the same direction as the outermost active portion of the saw blade, the radial projection of the latter is preferably zero, i.e. the saw blade is radially covered by the eccentric member. On the other hand, when the eccentric member is rotated to point towards the opposite radially outermost portion of the saw blade, the saw head is in the position of maximum range.

In the first situation referred to, the saw head together with the coaxial shafts is suited to be easily inserted into the inner space or canal of a hollow bone as the saw teeth (not moving) cannot contact the bone wall. Subsequently, rotating both shafts with respect to each other results in an increase of the radial range of the saw head as the saw blade comes out of the eccentric member. When the saw head then fits to the inner diameter of the hollow bone, the eccentric member and saw blade each engage the internal wall of the hollow head and the sawing operation may start.

The eccentric member engaging the inner wall defines an abutment for the blade such that forces acting in the cutting direction may be transmitted to the blade. The cutting operation is manually controlled by rotating the whole saw after fixing the shafts with respect to each other. The rotational position of the saw blade sector may be made visible by the way the sawing shaft is fixed in the holder. By stepwise releasing, rotating and refixing both shafts, the cutting depth is stepwise increased. A maximum cutting depth will be obtained when the eccentric member is positioned in opposed relation to the maximum radial extension of the saw blade with respect to the shaft. By returning the saw blade to the minimum position above referred to, the saw head may be drawn back and out of the hollow bone.

According to a preferred embodiment of the invention, both shafts are made flexible such that the shaft assembly may follow curvatures present in the hollow bone.

According to a further embodiment of the invention, a holding device is composed of a pair of members which are rotatably mounted, one member being secured to the saw shaft and the other member to the second shaft. One of the members is preferably formed as an adjusting plate which is connected to a handle to cooperate with a base plate. Still further, the inner shaft is fixed to the adjusting plate and the outer shaft is mounted in the base plate. The handle is rigidly mounted to the outer shaft. Rotating both shafts with respect to each other corresponds to rotating the adjusting plate with respect to the base plate.

In a further embodiment the adjusting plate may be fixed in indexing positions of the base plate by means of a fast acting locking element. Preferably, this is accomplished by indexing positions formed as holes in the base plate cooperating with a spring-biased indexing ball in the adjusting plate.

To facilitate handling, the invention further contemplates providing the base plate with a knurling wheel. Still further, the base plate may be provided with a scale which shows the rotational position of both plates in combination with a pointer provided on the adjusting plate.

Moreover, the location of the fast acting locking device on the adjusting plate may be selected such that it can be actuated by the hand engaging the handle. This facilitates a stepwise increasing of the cutting depth.

According to a further embodiment, both shafts are releasably mounted to replace the shafts in pairs fitting to each other. The outer shaft is preferably secured by a locking screw cooperating with a recess in the outer shaft. The shaft in the holder is preferably releasably secured by a spring-biased pin. The inner shaft is preferably provided with a flat portion close to its fixing end, wherein the flat portion is received in an elongated bore to non-rotatably mount this portion in the bore.

According to a further aspect of the invention, the coaxial shafts are guided in a gripping tube fixed in the holder. Preferably, the gripping tube is releasably mounted including a stop at its free end. The gripping tube facilitates applying the saw in a predetermined distance where the cutting is to be performed.

The gripping tube preferably comprises a pair of mutually movable tube portions of which one is fixed to the holder and the other one includes the stop. The tube portions cooperate through threads and may be locked in positions relative to each other by means of a locking nut provided on the inner tube portion by engaging a front end of the outer tube portion. Thereby the length of the gripping tube is varied to adjust a desired distance between the saw blade and the stop.

Still further, the outer tube portion includes a window for observing the position of a scale on the inner tube portion. An adjusting range between 100 and 200 mm, preferably 150 mm, is preferred for the bipartite tube. The gripping tube preferably is received in a bore of the holder and may have a peripheral groove cooperating with a locking screw or a spring-biased pin on the holder.

According to a further embodiment, the saw blade is provided with teeth located along a symmetrical arc. This feature allows continuous sawing in one rotational direction as well as an oscillating operation, for example, to divide predetermined segments of the bone cross section. It is particularly useful when the saw blade is mounted on the inner shaft.

According to a further embodiment the saw blade and/or the eccentric member are releasably connected to the shafts to be fit to different inner and outer diameters of the bone, In a further embodiment the eccentric member radially projects the outer edge of the saw blade in a predetermined position of the eccentric member. This facilitates a parallel guidance of the coaxial shaft towards the bone, the teeth of the sawing blade not contacting the bone wall.

The releasable mounting of the components of the saw allows sterilization of the components to fill the hygienic requirements for an operation. The surgeon may take the components from a set of different saw blades and different eccentric members, possibly even from different pairs of shafts and gripping tubes to obtain a tool which best fits the bone to be treated. Even when operating, the surgeon may change the saw blade and/or the eccentric member. This might be accomplished while not alternating the adjusted cutting position.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 3 is a front view partly in section of the saw of FIG. 1 along the line A—A;

FIG. 4 is an end view of the saw in FIG. 1 in the direction of arrow 4 pointing towards the saw blade end; and FIG. 5 is a side view of a saw handle in the direction of the arrow 5 in FIG. 2.

DESCRIPTION OF THE PREFERRED EMBODIMENT

Figure 1:
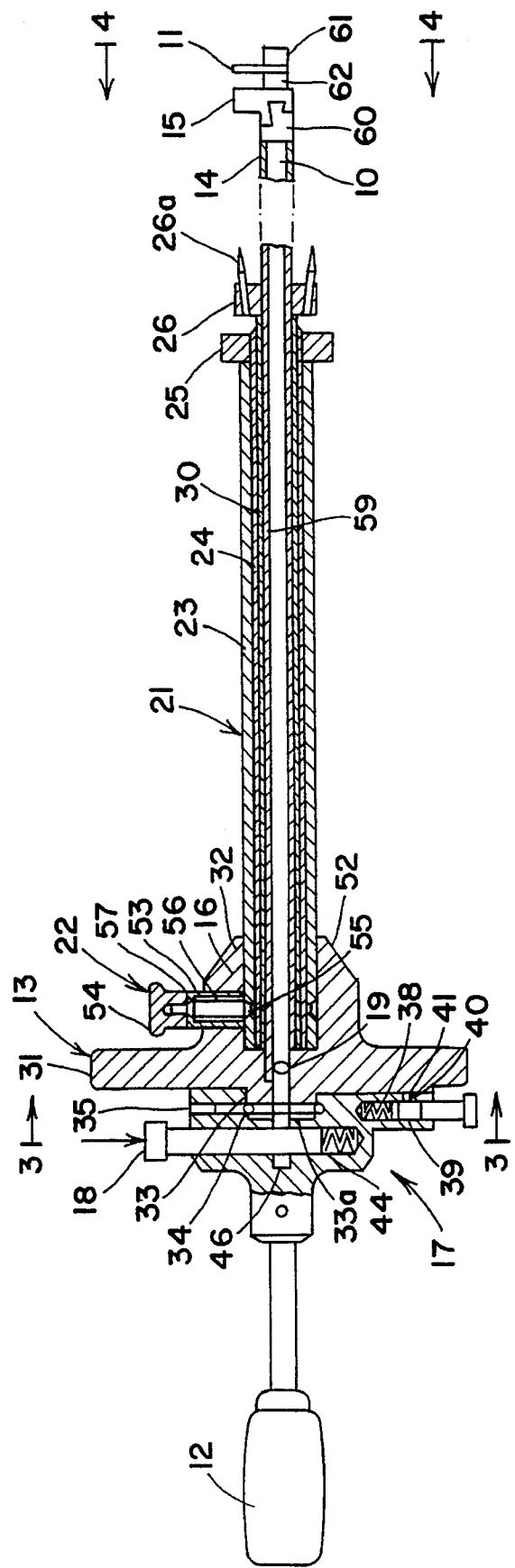
FIG. 1 is a longitudinal section of the surgical saw according to the invention.
Figure 2:
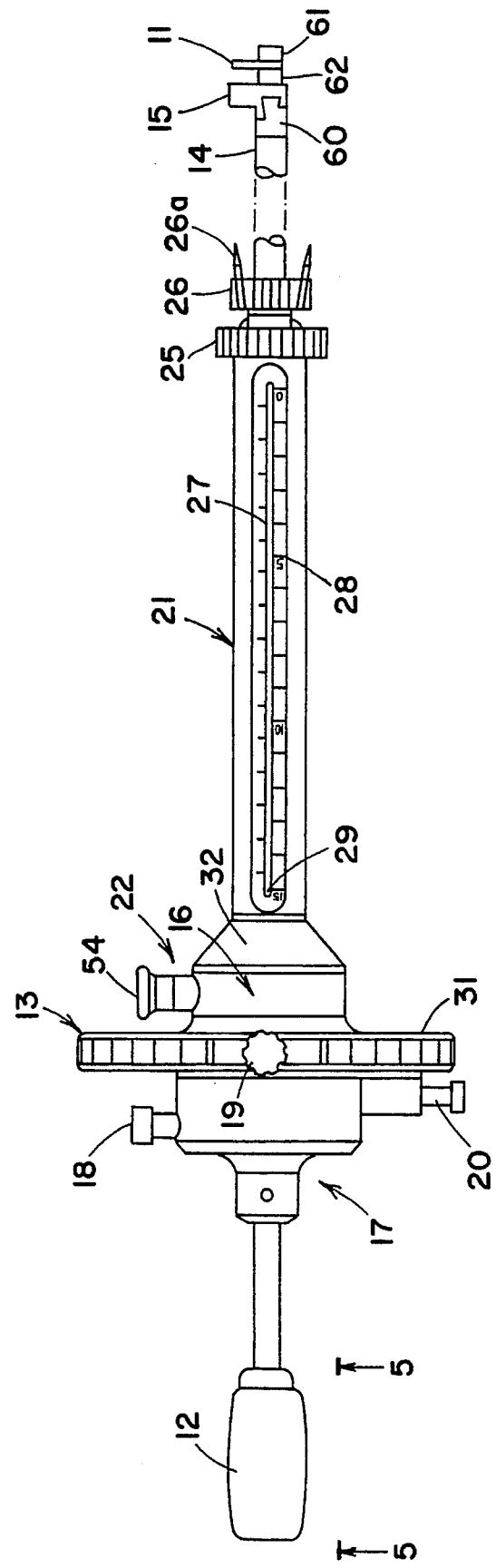
FIG. 2 is a side view of the saw shown in FIG. 1.

Referring to FIGS. 1 and 2, there is shown a surgical saw comprising an extended saw shaft 10 having an end to which a sector-shaped saw blade 11 is releasably secured. The shaft 10 extends through a base plate 16 of a holder 13 to be releasably mounted in an adjusting plate 17 of the holder 13 having a handle 12. A second shaft 14 is coaxially provided around the shaft 10 to which an eccentric member 15 is releasably mounted adjacent the saw blade and is fixed in the base plate 16. The base plate 16 and the adjusting plate 17 are mounted rotatably with respect to each other. The handle 12 is fixed to the adjusting plate 17.

The inner shaft 10 is fixed in the adjusting plate 17 but can be released by pressing down the spring-biased pin 18. A recess of the pin 18 (not shown in FIG. 1) cooperates with a suitable cross sectional shape of the shaft 10 to fix it against rotation and axial displacement. When the pin 18 is pressed down, the shaft 10 is freed. The outer shaft 14 is fixed in the base plate 16 by a locking screw 19. The adjusting plate 17 may be rotated with respect to the ground to the base plate 16 when the locking is released by pressing the spring-biased pin 20.

Both shafts 10, 14 are flexible and the shafts are guided within a gripping tube 21. The gripping tube 21 may be released from the base plate 16 by pulling a spring-biased knob 22. The gripping tube 21 is bipartite having an outer tube portion 23 and an inner tube portion 24 movable. The outer tube portion 23 is anchored in the base plate and cooperates with the inner tube portion 24 through a thread 30. By rotating the inner tube portion with respect to the outer tube portion the overall length of the gripping tube may be set to a desired length and may be locked by a locking nut 25. The free end of the inner tube portion 24 comprises a stop 26 including a pair of setting points 26a. The locking nut 25, the stop 26 and the fixing area of the outer shaft in the base plate 16 are provided each with a knurling edge. The outer tube portion has an elongate window 27 and a scale 28 adjacent thereto to make visible a marker 29 to indicate the position of the inner tube portion 24 with respect to the outer tube portion 23.

FIGS. 1 and 3 show in more detail the mounting of the shafts 23, 24 and of the gripping tube 21 on the holder 13 and how the adjusting plate 17 coacts with the base plate 16. The base plate 16 has a knurled disc-shaped portion 31 to fix the outer shaft, a portion 32 to fix the gripping tube and an axial flange 33 for mounting the adjusting plate 17.

The flange 13 cooperates with a circular recess 33a in the adjusting plate 17 and includes a peripheral groove defining a circular groove 34 in cooperation with a groove in the recess 33a. A radial threaded bore 35 opens into the groove 34. The adjusting plate 17 may be placed in alignment at the knurled edge portion 31 of the base plate, and can be locked thereto by means of balls placed through the threaded bore 35 in the circular peripheral groove 34. The threaded bore may be then closed by a screw. Thus a strong, but easily rotatable connection is provided between the adjusting plate and the base plate.

The peripheral knurled portion 31 carries a scale 36 to indicate the rotational position of the adjusting plate 17 with respect to the base plate 16. The locking mechanism between both plates 16, 17 is formed as a pointer-shaped portion 37 of the adjusting plate 17. A spring-biased pin 20 is pressed radially outwardly such that a tapered portion 39 of the pin 20 urges a ball 40 towards the knurled portion 31 of the base plate 16. The ball 40 may index into holes 41 in the knurled portion 31. The holes 41 are formed as small indentations having a diameter and a depth smaller than the diameter of the ball 40.

Displacing the pin 20 with respect to the spring 38 frees the ball 40 so that the adjusting plate 17 may be rotated with respect to the base plate 16. Then pin 20 is guided in a bore and secured by the ball 40. As the adjusting plate 17 is mounted on the axial flange 33 of the base plate 16 including the balls engaging the groove 34, the adjusting plate 17 can fully engage the knurled portion 31 of the base plate in any rotational position.

The inner shaft 10 is fixed in the adjusting plate 17 by a pin 18 biased by a spring 44. A portion of the shaft close to its fixing end is formed to be flat (FIG. 3). The flat portion is received in an elongate bore 45 having a shape to non-rotatably receive the flat shaft portion. In the fixed position, the spring 44 urges the pin 18 at a first end of the elongate bore 45 onto the saw shaft 10. For releasing, the pin 18 is radially urged toward the spring 44 to urge the spring onto the saw shaft 10 at a second end of the elongate bore 45. The second end of the elongate bore 45 is circular corresponding to the diameter of the saw shaft 10. Thus the cylindrical end 46 of the saw end 10 adjacent the flat portion of the saw shaft 10 towards the handle 11 is guided in the elongate bore 45. The cylindrical pin 18 is guided in a bore and secured against rotation and falling out by a locking pin engaging a longitudinal groove in the pin 18.

The axial length of the flat portion of the saw shaft 10 is the same as the diameter of the pin 18. For inserting the saw shaft 10 it is pushed into the holder 13 up to the stop while pressing the pin 18 at the same time. Then the pin 18 is released and the shaft is rotated. In the proper axial position of the shaft 10, the spring-biased pin 18 locks with the flat portion of the shaft 10 in the elongate bore 45, wherein the spring 44 is partly released. This defines a predetermined distance of the cutting blade 11 from the holder 13 or respectively the stop 26 in an axial direction.

The outer shaft is locked to the knurled portion 31 of the base plate 16 by a locking pin 19 including a knob accommodated in an indentation 50 of the knurled portion 31. The inner end of the outer shaft is provided with a recess coacting with the axial environment of the knurled portion 31 such that the outer shaft 14 is secured against rotation with respect to the base plate 16. The outer shaft 14 is fixed to the end portion by a locking pin 19 having a pointed tip engaging an indentation at the outer periphery of the end portion of the shaft 14.

The outer tube portion 23 of the gripping tube 21 is held in a portion 32 of the base plate reduced in diameter. This is accomplished by a spring-biased pin 22 engaging a peripheral groove 52 in the gripping tube. This facilitates a fast replacement of the gripping tube which does not have to be oriented in a predetermined angular position when being assembled.

The spring-biased pin 22 comprises a central bolt 53 including a pulling knob 54 at its outermost end and a projection 55 at the inner end. A spring 56 is supported on a sleeve 57 screwed in a bore of the base plate portion to urge the projection 55 towards an abutment on the inner wall of the portion 32. The pulling knob 54 has a diameter larger than that of the threaded sleeve 57. The threaded sleeve is aligned with respect to the periphery of the portion 32 so that the pulling knob 54 engages the threaded sleeve 57 as well as the base plate portion 32. The outer end of the knob 54 has an enlarged diameter to facilitate gripping and pulling outwardly against the force of the spring 56. Thus the bolt 57 is pulled out of the groove 52 in the gripping tube 51 which is thus released.

The inner tube portion 24 of the gripping tube 21 has a ring 59 defining the mark 29 visible through the window 27 to indicate the position of the inner tube portion.

The handle 12 is shape to suit a safe gripping of the sawing tool. Furthermore, the spring-biased pin 20 may be actuated at the same time, without letting loose the handle.

The saw head is described with reference to FIGS. 1, 2 and 4. FIG. 4 shows the knurled peripheral portions of the stop 26, the locking nut 25 and the wheel portion 31 of the base plate 16 as well as the circular periphery of the gripping tube mounting 32. For the sake of clarity the pin 20, the locking screw 19 and the pulling knob 54 are shown.

The end of the outer shaft 14 carries a holding member 60 for the eccentric member 15. The saw blade 11 is fixedly mounted on the inner shaft 10 by a nut 61. A space 62 is threaded on between the saw blade 11 and the eccentric member 15 which space is contacted by the saw blade fixed by the nut 61. The saw blade 11 and the eccentric member 15 are located under an angle of 90° with respect to the locking screw 19. The eccentric member is shaped as a circular disc which is eccentrically mounted on the shaft 14. The saw blade 11 projects from the shaft into a radial direction, but is symmetrical in shape. The preferred direction is shown by an arrow. However, the saw blade may be oscillated as well.

In the position of the blade and eccentric member as shown in FIG. 4, the eccentric member 15 completely covers the cutting blade 11. In this position, sawing is prevented. However, when the eccentric member 15 is rotated with respect to the saw blade 11 up to a maximum angle of 180°, the sawing blade 11 comes out of the shield of the eccentric member 15 and becomes gradually exposed.

The orientation of the adjusting plate with respect to the base plate of FIGS. 3 and 4 shows the position to assemble the coaxial shafts 10, 14 including the preassembled eccentric member 15 and cutting blade 11.

While several examples of the present invention have been described, it is obvious that many changes and modifications may be made thereunto, without departing from the spirit and scope of the invention.

We claim:

1. A surgical saw comprising an elongate saw shaft, a sector-shaped saw blade secured to said shaft and having a number of outer teeth, a holding means including a handle, said saw shaft rotatably mounted in said holding means, a second shaft also rotatably mounted in said holding means and mounted coaxially and exteriorly with respect to said saw shaft, both of said shafts being rotatable with respect to each other and lockable in predetermined angular positions in the holding means, said saw shaft being releasably locked to said holding means by a spring-biased pin and said second shaft being locked by means of a locking screw cooperating with a recess provided in said second shaft, an eccentric member mounted to a free end of the second shaft close to the saw blade; and the saw blade and the eccentric member extending radially outwardly a predetermined selected distance so that they can be inserted into a hollow bone, wherein the holding means comprises a pair of members comprising a base plate and an adjusting plate rotatably mounted and operatively connected with respect to each other, said adjusting plate being fixed to the saw shaft and said base plate being fixed to the second shaft, and wherein said adjusting plate is mounted to said handle, wherein the saw shaft includes a flat portion close to an end held by said holding means and wherein the flat portion is received in an elongate bore in said adjusting plate, said elongate bore being formed with a cross-section shape to non-rotatably receive said flat portion.

2. A surgical saw comprising an elongate saw shaft, a sector-shaped saw blade secured to said shaft and having a number of outer teeth, a holding means including a handle, said saw shaft rotatably mounted in said holding means, a second shaft also rotatably mounted in said holding means and mounted coaxially and exteriorly with respect to said saw shaft, both of said shafts being rotatable with respect to each other and lockable in predetermined angular positions in the holding means, said saw shaft being releasably locked to said holding means by a spring-biased pin and said second shaft being locked by means of a locking screw cooperating with a recess provided in said second shaft, an eccentric member mounted to a free end of the second shaft close to the saw blade; and the saw blade and the eccentric member extending radially outwardly a predetermined, selected distance so that they can be inserted into a hollow bone, wherein the holding means comprises a pair of members comprising a base plate and an adjusting plate rotatably mounted and operatively connected with respect to each other, said adjusting plate being fixed to the saw shaft and said base plate being fixed to the second shaft, and wherein said adjusting plate is mounted to said handle, wherein the saw shaft and second shaft are guided in a gripping tube fixed to the holding means, wherein the gripping tube is releasably mounted to the holding means by a fixing portion, wherein the gripping tube has a free end and includes a stop at said free end, wherein the gripping tube comprises a first and a second tube portions movable with respect to each other, said first tube portion being fixedly secured to the holding means and said second tube portion including said stop, wherein the first and second tube portions are threaded to each other and can be locked in relative positions with respect to each other by means of a locking nut provided on the first tube portion to engage a front end of the second tube portion.

3. The surgical saw of claim 2 wherein the second tube portion includes a window for observing the position of a marking provided on the first tube portion.

4. The surgical saw of claim 3 wherein a scale is provided adjacent the window.

5. The surgical saw of claim 4 wherein the tube has an adjusting range of between 100 mm and 200 mm.

* * * * *